US006681407B2

(12) United States Patent
Martz

(10) Patent No.: US 6,681,407 B2
(45) Date of Patent: Jan. 27, 2004

(54) WAISTLESS UNDERWEAR ALTERNATIVE SECRET PANTS SHIELD

(76) Inventor: Christine Martz, 1128 Ruth Pl., North Bellmore, NY (US) 11710

( * ) Notice: Subject to any disclaimer, the term of this patent is extended or adjusted under 35 U.S.C. 154(b) by 0 days.

(21) Appl. No.: 10/202,350

(22) Filed: Jul. 24, 2002

(65) Prior Publication Data

US 2003/0233701 A1 Dec. 25, 2003

Related U.S. Application Data

(60) Provisional application No. 60/390,939, filed on Jun. 24, 2002.

(51) Int. Cl.[7] ................................................. A41B 9/00
(52) U.S. Cl. ........................ 2/400; 2/46; 2/402; 2/406; 2/408
(58) Field of Search ............................... 2/46, 400, 402, 2/406, 408; 128/891; 604/354, 358, 370, 385.01, 385.03, 385.05, 385.14, 385.21, 385.23, 386, 374, 387, 389, 393, 400, 402

(56) References Cited

U.S. PATENT DOCUMENTS 4,333,466 A  *  6/1982  Matthews ............... 604/385.01
4,648,876 A  *  3/1987  Becker et al. ............... 604/370
4,955,880 A  *  9/1990  Rodriquez ................... 604/393
5,388,275 A  *  2/1995  Oram ............................ 2/406
5,807,365 A  *  9/1998  Luceri ........................ 604/367
6,497,688 B2 * 12/2002  Lasko ......................... 604/367

OTHER PUBLICATIONS

True Fit Try On® garment liners Internet page, www.truefittryon.com 3 pages, showing liners.*

* cited by examiner

*Primary Examiner*—Gloria M. Hale
(74) *Attorney, Agent, or Firm*—Alfred M. Walker

(57) ABSTRACT

A women's waistless and seamless clothing adherable underwear includes an oval pad made of a soft absorbent material, wherein the pad has double sided strips of adhesive tape with removable peel-off cover strips to attach to the inside crotch area of low slung clothing pants, such as tight pants, leotards or dungaree jeans facing upward to the skin and crotch of the wearer. The material is preferably a soft, non-woven, absorbent material. The underwear is particularly suited for women who wear tight pants, or low waist hip hugger pants, which widely reveal waist bands and seams of panty underwear, or expose underwear waist bands. The underwear is minimally intrusive and is attractive for women who like to wear jeans without underwear but who fear bacterial infection or exposure to clothing dyes or irritating stitching.

9 Claims, 3 Drawing Sheets

WAISTLESS UNDERWEAR ALTERNATIVE SECRET PANTS SHIELD

This application claims the benefit of Provisional Application Ser. No. 60/390,939 filed Jun. 24, 2002.

FIELD OF THE INVENTION

The present invention relates to disposable waistless and seamless underwear for women.

BACKGROUND OF THE INVENTION

Conventional women's panty underwear with waistbands and seams around the leg openings is unsuitable for women who wear tight pants, or low waist pants (such as "hip huggers"), which openly reveal waist bands and seams of panty underwear, or expose underwear waist bands.

Moreover, for women who like to wear jeans without underwear there is a natural fear of bacterial infection or exposure of sensitive body tissues to clothing dyes or irritating stitching.

Among related prior art patents are those which fall into four categories for which common distinguishing arguments can be composed. The categories are special garments or undergarments, absorbent materials for pads, clothing adhered pads, and maternity wear.

Clothing Adhered Pads:

U.S. Pat. No. 6,162,457 of the Applicant Christine Martz herein describes small clothing adherable perfume patches which attach to the inside of clothing, such as a blouse, with a skin facing side rubbing intermittently against the skin, to mute the smell of the perfume emitted by exposure to body oil in the skin of the wearer.

However, neither Martz '457 nor Williams, in U.S. Pat. No. 5,729,835, relate to a pants shield designed to permit the user to comfortably wear jeans, pants or shorts or the like without an undergarment and also without any external indication that such a shield is being used. Martz '457 relates to small garment pads used to emit a fragrance; their general physical shape and construction are different from the instant invention. Williams '835 relates to a panty liner of generally oblong configuration specifically for use with thong underwear. The multilayer construction designed for maximum absorption and a "penetration barrier" would be far too bulky for the objectives of the present invention.

Maternity Wear:

Blair, in U.S. Pat. No. 5,946,730 describes an expansion panel for temporarily providing a larger waist and frontal area so that a user can wear the jeans during pregnancy. The panel is easily removable when it is no longer needed. Clearly this prior art is irrelevant to the present invention.

Absorbent Materials for Pads:

Palumbo et al., in U.S. Pat. No. 6,232,250 B1 relates to an absorbent pad with defined fluid receiving and fluid retention regions. It is designed primarily for use in treating female incontinence.

Rock et al., in U.S. Pat. No. 5,344,698 describes a composite undergarment fabric of multilayer construction using a skin contact layer of hydrophilic material with superabsorbent and high moisture transmission layers attached.

Mende, in U.S. Pat. No. 5,242,632 relates to a nonwoven fabric and manufacturing method. It is a soft bulky absorbent and permeable material.

Tanner et al., in U.S. Pat. No. 6,162,961 has an absorbent article having exceptional expansion properties when wetted.

None of the above materials are required in the construction of the present invention. High moisture absorption is not a key requirement. Comfort and low thickness so as to preclude edge detection from external viewing of the outer garment are principal requirements which cannot be supported by the materials described in this group of patents.

Special Garments or Undergarments:

Glaug, in U.S. Pat. No. 6,307,120 B1 describes a cloth-like, breathable disposable brief with refastening means. It is an adult garment for controlling incontinence.

Davis, in U.S. Pat. No. 5,832,535 discloses a genital covering garment that is a minimum temporary covering generally useful for surgical procedures or examinations not requiring visual or tactile access to these regions.

Marbach, in U.S. Pat. No. 3,339,208 relates to a minimal covering for the lower part of the anatomy consisting of a spring supported patch that fits between the user's legs and engages the pubic bone and the sacrum. The intended use is as a bathing brief.

Crawford, II, in U.S. Pat. No. 5,467,482 describes a self supporting sideless and waistless tanning brief. This is a malleable wire frame with a cloth covering extending to the rear with a spring member which fits between the buttocks of the wearer.

Vargason, in U.S. Pat. No. 5,903,922 discloses a removable undergarment that is designed for quick wearing. A variety of attachment patches are used to attach the undergarment around the user in a comfortable fashion.

Lampman, in U.S. Pat. No. 4,905,323 describes a disposable undergarment held by a partially encircling belt, wherein the undergarment covers the pubic area and central buttocks of the user. It can be used by women while trying on bathing suits or the like in stores.

The inventions in this group relate to garments or undergarments. None disclose a clothing attached secret shield that can be used as a substitute to using an undergarment.

OBJECTS OF THE INVENTION

It is therefore an object of the present invention to provide underwear for women which is suitable for wearing with low slung hip hugging pants and the like.

It is also an object of the present invention to provide waistless and seamless underwear for garments which utilizes a sanitary absorbent material and which prevents irritation or exposure to bacteria and other pathogens.

Other objects which become apparent from the following description of the present invention.

SUMMARY OF THE INVENTION

In keeping with these objects and others which may become apparent, the present invention is a pants shield that is invisible from the exterior and which can be used with any form-fitting attire without the use of underpants or any undergarment.

Since the pants shield is adherable only to the upper crotch facing area of an outer pants garment, it is unencumbered by auxiliary supports, such as annoying skin adhering adhesives or other body supports, such as waistbands, belts, or buttocks holding supports.

Some current fashions for young women are such that they render normal underpants or even thongs undesirable, but the alternative of not wearing underwear has its own disadvantages.

Constructed of a thin absorbent pad, the pants shield of the present invention is adhesively bonded temporarily during use to the crotch area of the outer garment. It can be used in jeans, exercise pants, leotards, shorts, or any normal pants. This permits active use of the garment without underpants which introduce seams and hems that show through as panty lines. This secret pants shield is more comfortable than a thong and more fashionable because low cut pants often reveal the top band of the thong when bending or stretching. Because of the soft shield surface in contact with vaginal area, it prevents infections that can arise from abrasion or irritation caused by rubbing against clothing materials when underpants are not worn. The shield of this invention provides a clean bacteria-free barrier from garment fabric which may also contain irritating dyes. It absorbs small amounts of moisture and also provides extra protection for garments during menstruation periods without the need for an undergarment.

Therefore this secret pants shield permits sanitary wear of pants without underwear providing the ultimate fashion compatibility with any pants attire. Comfort is provided by the soft contact material. Since it is securely bonded with a temporary adhesive, it can be used for active pursuits. The disposable nature and small compact size makes it convenient to change a shield whenever it gets messy. The secret pants shields are available in different sizes such as small, medium, and large. They are also available in colors so as not to contrast with the color of pants which may be shear or slightly transparent.

BRIEF DESCRIPTION OF THE DRAWINGS

The present invention can best be understood in connection with the accompanying drawings. It is noted that the invention is not limited to the precise embodiments shown in drawings, in which.

DETAILED DESCRIPTION OF THE INVENTION

Figure 1:
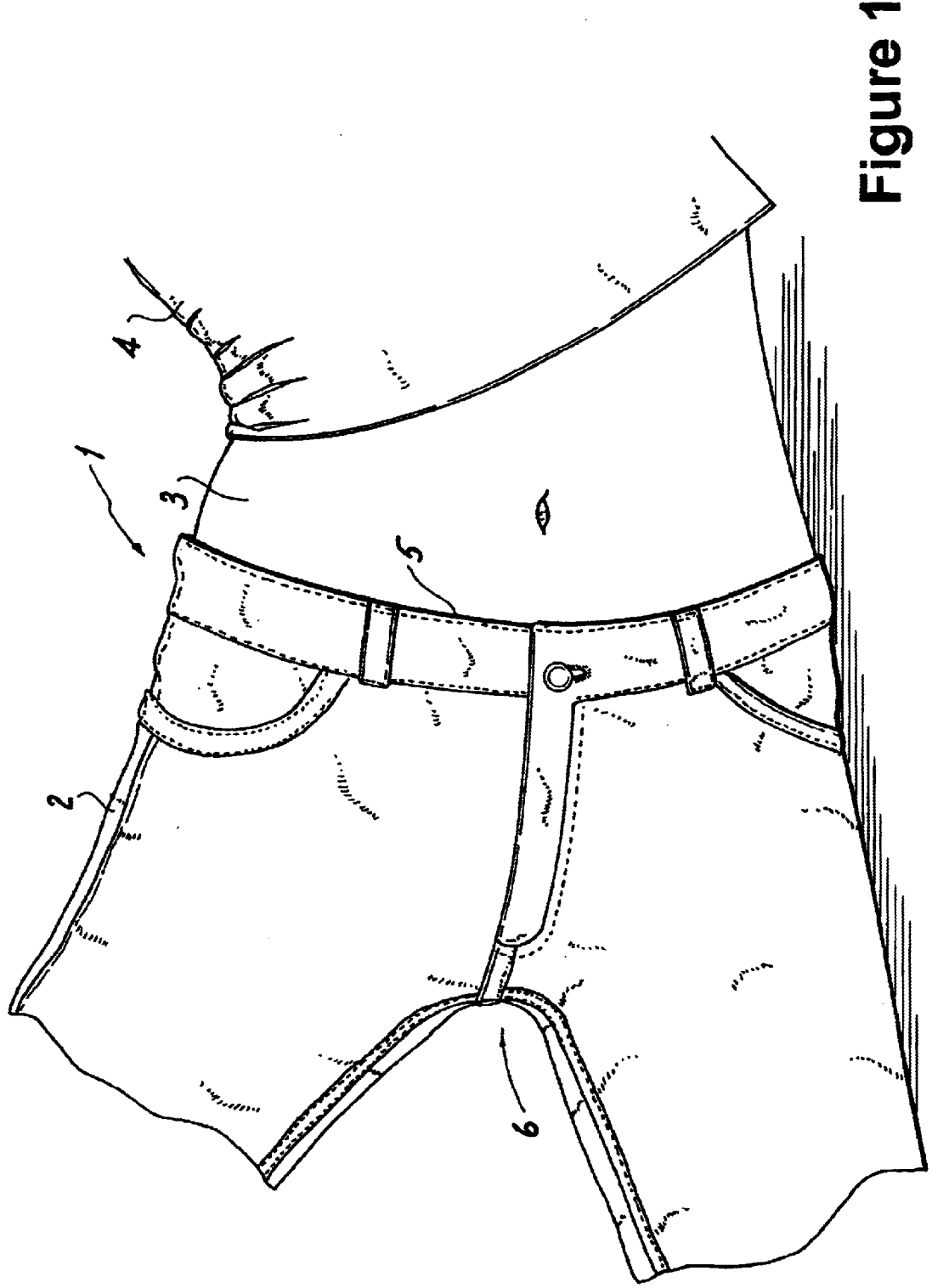
FIG. 1 is a partial perspective view of a reclining woman wearing form-fitting jeans.

FIG. 1 shows a detail of a reclining woman 1 wearing an ensemble which derives maximum benefit from the secret pants shield of this invention. Several features of the style conspire to make the use of underwear undesirable. Jeans 2 are tight and form-fitting with low hip-hugging waist band 5. The short top 4 leaves a bare abdominal midriff 3. This exposed central area is antithetical to underwear waistbands. The site of the secret pants shield of this invention is crotch area 6 which is not disturbed by any indication of the shield within.

Figure 2:
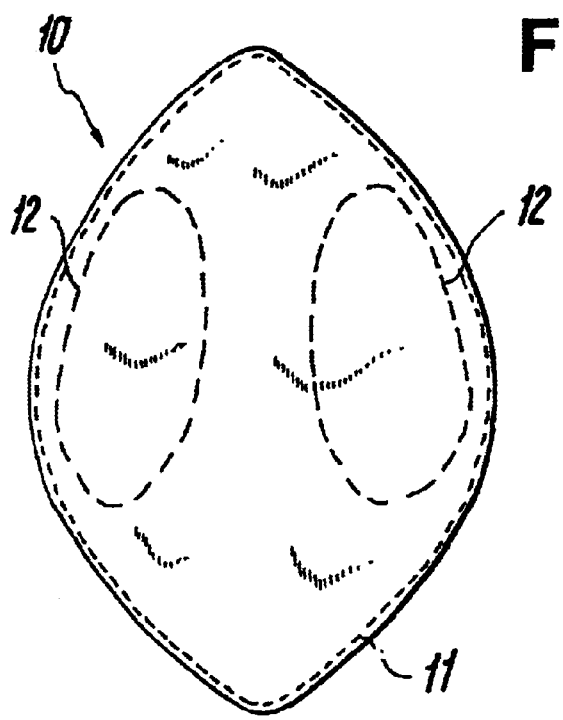
FIG. 2 is a top view of a secret pants shield of this invention.

FIG. 2 shows pants shield pad 10 with circumferentially extending bonded edge 11 and bottom adhesive areas 12. While FIG. 2 shows two bottom adhesive areas, one or more adhesive areas can be employed to adhere pants shield pad 10 to an inside crotch facing portion of a pants garment.

Figure 3:
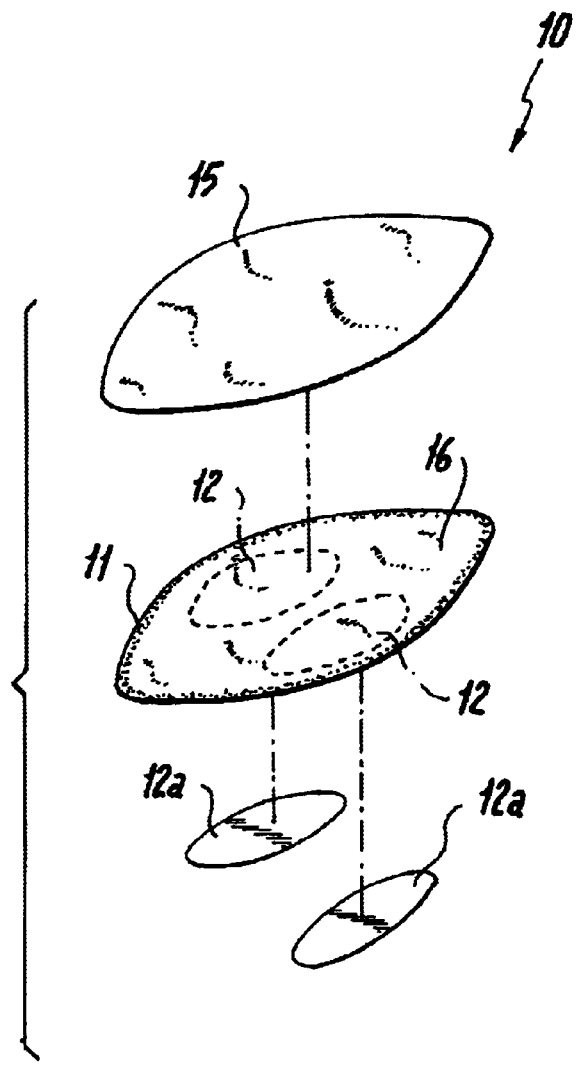
FIG. 3 is an perspective exploded view of the pants shield of FIG. 2.

The exploded view of FIG. 3 reveals the construction with top layer 15, adhesive ring 11 around bottom layer 16, adhesive areas 12 and release liners 12a which cover adhesive patches 12 until use. The top layer 15 is a soft absorbent paper material such as soft paper towel, or of a synthetic plastic fabric material. The bottom layer 16 can be identical material. Adhesive ring 11 bonds layers 15 and 16 permanently. Adhesive 12 is a temporary adhesive analogous to that used on feminine hygiene panty liner pads. An alternate construction of a single layer equivalent to the two layers of soft paper towel can also be used. Moreover, one or more adhesive layers 12 can be employed to attach pants shield pad 20 to a crotch facing area of pants garment.

A prototype for one embodiment for a secret pants shield has been constructed and tested successfully. Layers 15 and 16 were cut out of KLEENEX® VIVA® paper towel, and the adhesive areas 12 were double width lengths of ¾" wide SCOTCH® Poster Tape from 3M Company.

Figure 4:
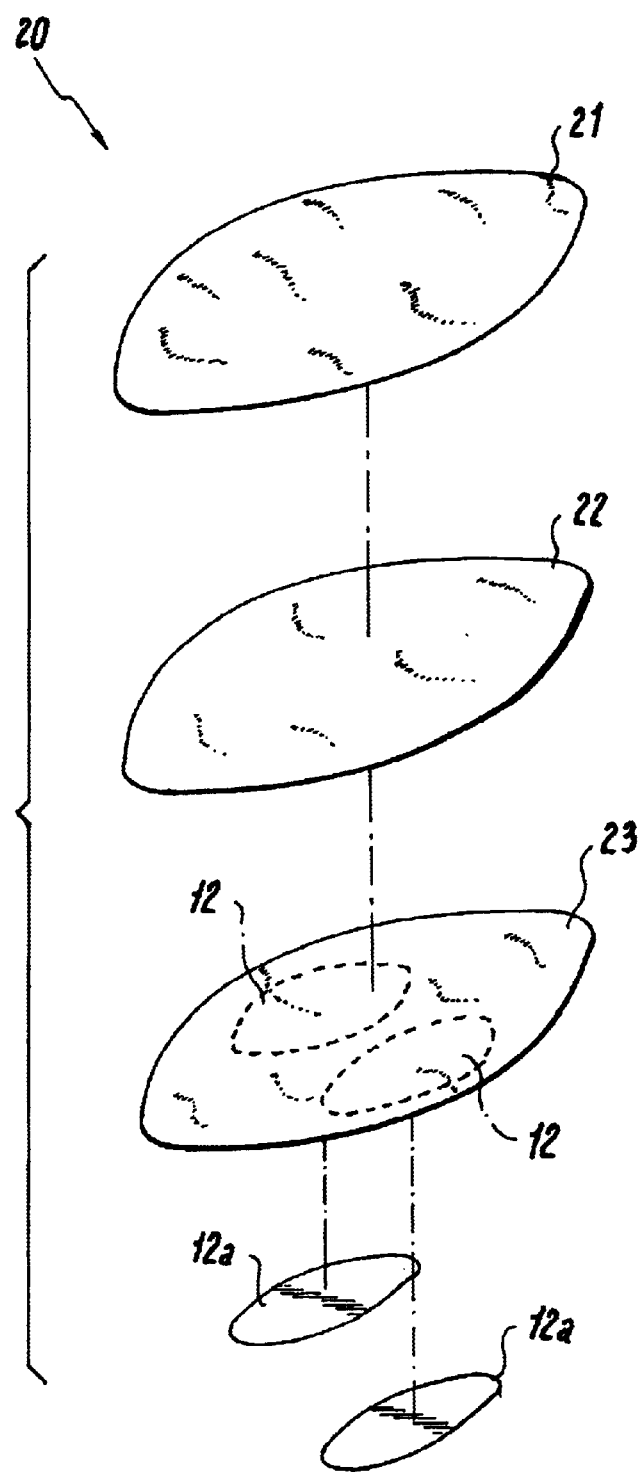
FIG. 4 is a perspective exploded view of a different embodiment of a pants shield.

FIG. 4 shows the construction of alternate embodiment 20 of the secret panty shield of this invention. It includes at least three surface bonded layers with adhesive patches on the bottom layer. Top layer 21 is a thin permeable nonwoven fabric material, such as of a paper or a synthetic plastic material. Middle layer 22 is a thin absorbent non-woven material, and bottom layer 23 is a thin impermeable layer, such as of paper or of a synthetic plastic. Adhesive patches 12 with release liners 12a complete shield 20. The construction and materials of the various layers are similar to those of a light weight bed pad.

The bottom layers 16 or 23 adjacent to the transparent temporary adhesive patches 12 can be selected in a variety of colors to minimize contrast with pants material.

Total thickness of the secret pants shield must be kept to a minimum to prevent a visible outline from showing through. For context, it is well to know that panty shields range from a thickness of about 0.08" (2 mm) to about 0.12" (3 mm) and are quite visible under tight pants. A LIGHT-DAYS™ feminine hygiene pad from KOTEX® is 0.075" (1.9 mm). The thickness of the preferred embodiment of secret pants shield as in FIG. 3 (with two layers) is about 0.030" (0.76 mm). The thickness of the second embodiment as in FIG. 4 (with three layers) is 0.025" (0.64 mm). The secret pants shield of this invention is therefore preferably less than 1 mm thick, which is not visible externally.

In the foregoing description, certain terms and visual depictions are used to illustrate the preferred embodiment. However, no unnecessary limitations are to be construed by the terms used or illustrations depicted, beyond what is shown in the prior art, since the terms and illustrations are exemplary only, and are not meant to limit the scope of the present invention.

It is further known that other modifications may be made to the present invention, without departing from the scope of the invention.

I claim:

1. The combination of an outer pants garment and a pad for use in lieu of a panty consisting essentially of:

a pad having sanitary absorbent material on a body facing side and an adhesive layer on an outer pants garment facing side temporarily affixed to a crotch area of said outer pants garment;

said pad being oval in configuration, with a wider midportion than ends of said pad to correspond to a vaginal area of a wearer;

said pad having a thickness of less than 1 mm. so as to prevent a visible outline from showing through said outer pants garment; and said pad bearing a color matching a color of said outer pants garment.

2. The combination of an outer pants garment and a pad as in claim 1 wherein said pad includes a bonded edge adhesive ring about the perimeter of said pad bonding a bottom layer to a top layer.

3. The combination of an outer pants garment and a pad as in claim 1 wherein said top layer and said bottom layer are of a soft absorbent paper material.

4. The combination of an outer pants garment and a pad as in claim 1 wherein said pad includes at least three surface bonded layers with said adhesive layer being at least one patch on a bottom layer thereof, said pants shield pad including:

a. top layer of permeable nonwoven fabric, b. a middle layer of absorbent non-woven layer, c. a bottom layer of an impermeable layer,
said adhesive patch having a release liner.

5. The combination of an outer pants garment and a pad as in claim 4 wherein said top layer and said bottom layer are of a soft absorbent plastic material.

6. The combination of an outer pants garment and a pad as in claim 4 wherein said top layer and said bottom layer are of a soft absorbent paper material.

7. The combination of an outer pants garment and a pad as in claim 1 wherein the thickness of said secret pants shield is about 0.030 inches (0.76 mm).

8. The combination of an outer pants garment and a pad as in claim 1 wherein the thickness of said secret pants shield is about 0.025 inches (0.64 mm).

9. The combination of an outer pants garment and a pad as in claim 1 wherein said pad bears a color matching a color of sad outer pants garment.

* * * * *